(12) United States Patent
Yamada

(10) Patent No.: US 8,436,320 B2
(45) Date of Patent: May 7, 2013

(54) FLUORESCENCE DETECTING APPARATUS, AND FLUORESCENCE DETECTING METHOD

(75) Inventor: Masayuki Yamada, Toyonaka (JP)

(73) Assignee: Konica Minolta Sensing, Inc., Osaka (JP)

( * ) Notice: Subject to any disclaimer, the term of this patent is extended or adjusted under 35 U.S.C. 154(b) by 1091 days.

(21) Appl. No.: 12/319,924

(22) Filed: Jan. 14, 2009

(65) Prior Publication Data

US 2009/0179159 A1 Jul. 16, 2009

(30) Foreign Application Priority Data

Jan. 16, 2008 (JP) .................................. 2008-007266

(51) Int. Cl.
*F21V 9/16* (2006.01)
(52) U.S. Cl.
USPC ...................................... 250/458.1; 250/459.1
(58) Field of Classification Search ............... 250/459.1, 250/458.1
See application file for complete search history.

(56) References Cited

U.S. PATENT DOCUMENTS

| | | | |
|---|---|---|---|
| 6,212,425 B1 | 4/2001 | Irion et al. | |
| 6,571,118 B1 | 5/2003 | Utzinger et al. | |
| 7,283,858 B2 * | 10/2007 | Sendai | 600/407 |
| 2002/0035330 A1 | 3/2002 | Cline et al. | |
| 2003/0050532 A1 | 3/2003 | Doguchi | |
| 2003/0191368 A1 * | 10/2003 | Wang et al. | 600/160 |
| 2004/0147843 A1 | 7/2004 | Bambot et al. | |
| 2005/0182321 A1 | 8/2005 | Frangioni | |
| 2008/0097198 A1 | 4/2008 | Miwa et al. | |
| 2011/0121200 A1 * | 5/2011 | Watanabe | 250/458.1 |

FOREIGN PATENT DOCUMENTS

| | | |
|---|---|---|
| JP | 2000-354583 | 12/2000 |
| JP | 2000-354583 A | 12/2000 |
| JP | 2002-500907 A | 1/2002 |
| JP | 2003-079570 | 3/2003 |
| JP | 2003-126015 A | 5/2003 |
| JP | 2003-190103 A | 7/2003 |
| JP | 2005-046634 A | 2/2005 |
| JP | 2006-014868 | 1/2006 |
| JP | 2006-122131 | 5/2006 |
| JP | 2006-317406 A | 11/2006 |
| JP | 2007-167325 A | 7/2007 |
| JP | 2008259595 A * | 10/2008 |

* cited by examiner

*Primary Examiner* — Christine Sung
(74) *Attorney, Agent, or Firm* — Brinks Hofer Gilson & Lione

(57) ABSTRACT

A fluorescence detecting apparatus includes: an excitation light emitter for emitting excitation light exciting a fluorescent material onto a measurement object; an illumination light emitter for emitting illumination light onto the measurement object; an image pickup device for sensing light from the measurement object; and a controller for controlling the image pickup device, the excitation light emitter, and the illumination light emitter. The excitation light is emitted from the excitation light emitter onto the measurement object to define an image pickup condition of the image pickup device, based on an image pickup result to be obtained by sensing light from the measurement object by the image pickup device. A light amount of the illumination light to be emitted from the illumination light emitter is set depending on the image pickup condition. The excitation light, and the illumination light of the set light amount are simultaneously emitted from the excitation light emitter and the illumination light emitter, to cause the image pickup device to sense light from the measurement object.

19 Claims, 6 Drawing Sheets

FLUORESCENCE DETECTING APPARATUS, AND FLUORESCENCE DETECTING METHOD

This application is based on Japanese Patent Application No. 2008-7266 filed on Jan. 16, 2008, the contents of which are hereby incorporated by reference.

BACKGROUND OF THE INVENTION AND RELATED ART STATEMENT

1. Field of the Invention

The present invention relates to a fluorescence detecting apparatus, and a fluorescence detecting method.

2. Description of the Related Art

Fluorescence is emitted from a fluorescent material when excitation light is emitted onto the fluorescent material. Heretofore, there have been reported various fluorescence detecting apparatuses for detecting the position of a specific portion with respect to an object to be measured (hereinafter, called as a "measurement object") by impregnating a fluorescent material into the measurement object, and sensing fluorescence to be emitted from the measurement object irradiated with excitation light. In the fluorescence detecting apparatuses, it is necessary to obtain an entire image of the measurement object, as well as a fluorescent image, in order to detect the position of a specific portion with respect to the measurement object. However, an image pickup condition i.e. an exposure condition such as a shutter speed and an aperture differs between a case where an image of a measurement object is obtained, and a case where a fluorescent image is obtained. Accordingly, it is not easily to display a fluorescent image and a measurement object image on an identical display screen. In the following, some of the conventional fluorescence detecting apparatuses are described.

For instance, Japanese Unexamined Patent Publication No. 2006-122131 (D1) discloses an apparatus provided with an image pickup device for capturing a fluorescent image, and an image pickup device for capturing an entire image of a measurement object. Image pickup operations are performed individually in respective optimum image pickup conditions by the image pickup devices. After the image pickup operations, the position of the fluorescent portion with respect to the entirety of the measurement object is detected by combining the fluorescent image and the measurement object image.

Japanese Unexamined Patent Publication No. 2006-14868 (D2) discloses a single image pickup device. The image pickup device is operable to sequentially capture a fluorescent image and an entire image of a measurement object in respective optimum image pickup conditions with a time lag. After the image pickup operations, the position of the fluorescent portion with respect to the entirety of the measurement object is detected by combining the fluorescent image and the measurement object image.

Japanese Unexamined Patent Publication No. 2000-354583 (D3) discloses a single image pickup device. The image pickup device is operable to simultaneously capture a fluorescent image and an entire image of a measurement object. In capturing the measurement object image, the light amount of illumination light is reduced by attaching a filter to an illumination light source for illuminating the measurement object. This enables to simultaneously capture a fluorescent image and a measurement object image without a likelihood that a fluorescent image may not be distinguished from the measurement object image. In other words, attaching a filter to the illumination light source for illuminating a measurement object enables to define an image pickup condition optimum for capturing both a fluorescent image and a measurement object image. The position of the fluorescent portion with respect to the entirety of the measurement object is detected based on an image captured by the image pickup device.

Japanese Unexamined Patent Publication No. 2003-79570 (D4) discloses a single image pickup device. The image pickup device is operable to capture a fluorescent image and an entire image of a measurement object with a time lag. After the image pickup operations, the position of the fluorescent portion with respect to the entirety of the measurement object is detected by combining the fluorescent image and the measurement object image. The image pickup device is also operable to capture a fluorescent image and an entire image of a measurement object in respective optimum image pickup conditions by changing a charge multiplication ratio of the image pickup device depending on a receiving light amount. After the image pickup operations, the position of the fluorescent portion with respect to the entirety of the measurement object is detected by combining the fluorescent image and the measurement object image.

The apparatus disclosed in D1 has two image pickup devices. Accordingly, the size and the cost of the apparatus may be increased.

The image pickup device disclosed in D2 captures a fluorescent image and a measurement object image with a time lag. Accordingly, in the case where the measurement object is moved in a time between the image pickup operations, positional displacement may occur between the fluorescent image and the measurement object image.

In the image pickup device disclosed in D3, the light amount of illumination light is reduced by attaching a filter. However, the reduced amount of illumination light is unchanged. Accordingly, there is a likelihood that a fluorescent image may not be distinguished from a measurement object image, depending on the intensity of fluorescence.

Similarly to the image pickup device in D2, the image pickup device disclosed in D4 captures a fluorescent image and a measurement object image with a time lag. Accordingly, in the case where the measurement object is moved in a time between the image pickup operations, positional displacement may occur between the fluorescent image and the measurement object image. Also, since the charge multiplication ratio of the image pickup device is predefined, a desirable image may not be obtained depending on a measuring condition.

SUMMARY OF THE INVENTION

In view of the above, it is an object of the present invention to provide a compact and inexpensive fluorescence detecting apparatus that enables to accurately detect the position of a fluorescent material with respect to a measurement object, using an image.

It is another object of the invention to provide a fluorescence detecting method that enables to accurately detect the position of a fluorescent material with respect to a measurement object easily and at a low cost.

A fluorescence detecting apparatus according to an aspect of the invention is operable to emit excitation light onto a measurement object to define an image pickup condition of an image pickup device based on an image pickup result to be obtained by sensing light from the measurement object irradiated with the excitation light; and then is operable to simultaneously emit excitation light and illumination light onto the measurement object to cause the image pickup device to sense light from the measurement object irradiated with the excitation light and the illumination light. The above arrangement is advantageous in providing a fluorescence detecting apparatus that enables to accurately detect the position of a fluorescent material with respect to a measurement object, using an image, at a reduced size and cost.

These and other objects, features and advantages of the present invention will become more apparent upon reading the following detailed description along with the accompanying drawings.

DETAILED DESCRIPTION OF THE PREFERRED EMBODIMENTS OF THE INVENTION

Figure 1:
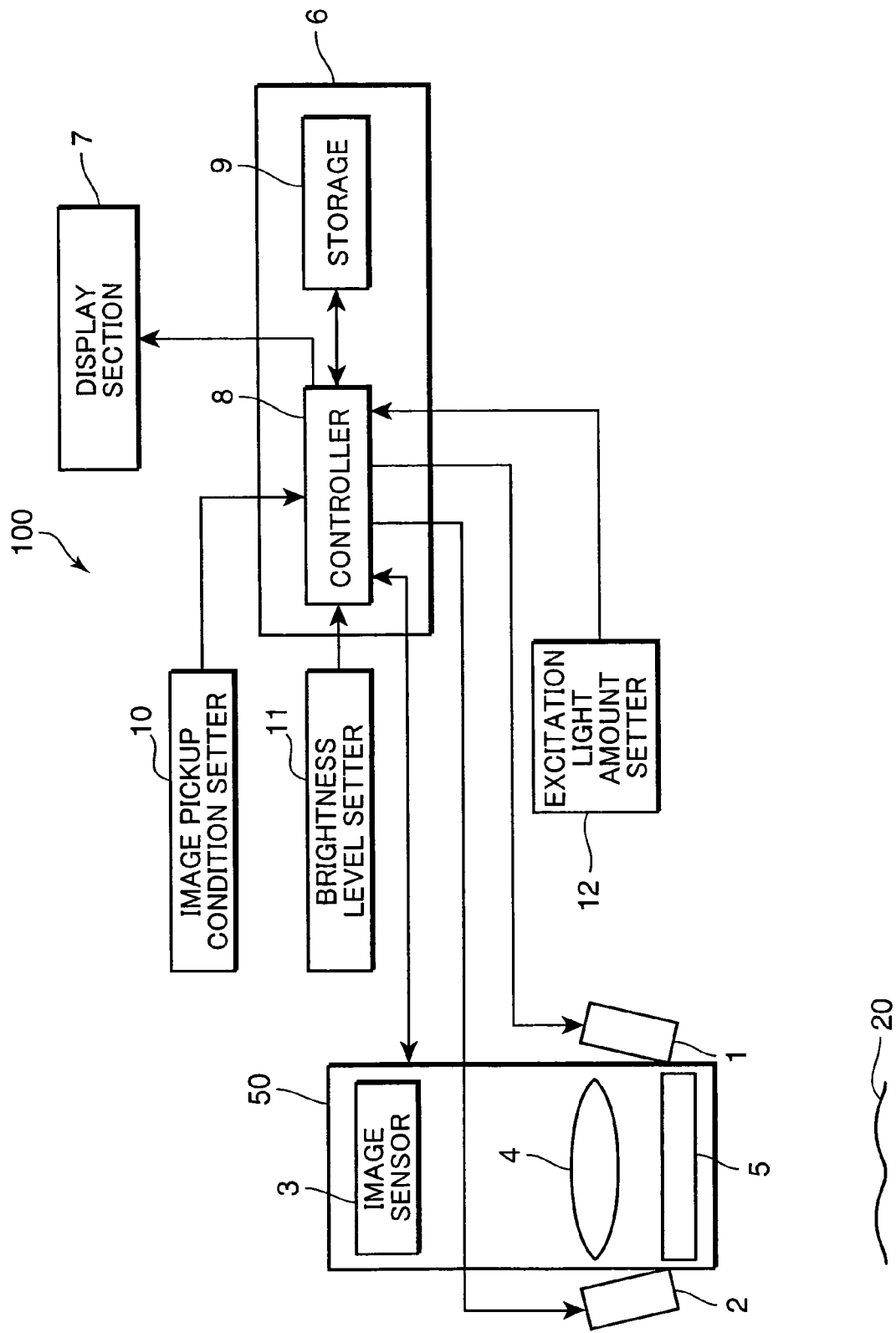
FIG. 1 is a diagram showing an arrangement of a fluorescence detecting apparatus embodying the invention.

In the following, an embodiment of the invention is described referring to the drawings. Elements having the same reference numerals throughout the drawings indicate identical or substantially equivalent elements, and repeated description thereof is omitted herein.

A fluorescence detecting apparatus embodying the invention is adapted to detect the position of a specific portion with respect to a measurement object. Specifically, the fluorescence detecting apparatus is operable to simultaneously emit excitation light exciting a fluorescent material, and illumination light onto a measurement object including a specific portion where the fluorescent material resides to sense light from the measurement object irradiated with the excitation and the illumination light in an optimum image pickup condition. This arrangement enables to sense fluorescence to be emitted from the fluorescent material irradiated with the excitation light, and reflection light from the measurement object so as to detect the position of the fluorescent portion with respect to the measurement object i.e. the position of the specific portion, based on an obtained image.

Arrangement on Embodiment

In this section, an arrangement on the embodiment is described.

FIG. 1 is a diagram showing an arrangement of a fluorescence detecting apparatus embodying the invention.

As shown in FIG. 1, a fluorescence detecting apparatus 100 embodying the invention includes an excitation light emitter 1, as a light source for emitting excitation light exciting a fluorescent material, an illumination light emitter 2 for illuminating the entirety of a measurement object 20 containing a fluorescent material, an image pickup device 50 for sensing light from the measurement object 20, a personal computer 6 equipped with a controller 8 and a storage 9, and a display section 7 for displaying an image. The fluorescence detecting apparatus 100 further includes an image pickup condition setter 10 for allowing the operator to set an intended image pickup condition, a brightness level setter 11 for allowing the operator to set a targeted pixel output value, and an excitation light amount setter 12 for allowing the operator to set an intended light amount of excitation light to be emitted from the excitation light emitter 1.

The excitation light emitter 1 is a light source for emitting excitation light exciting a fluorescent material. Examples of the excitation light emitter 1 include a laser and an LED (Light Emitting Diode). In the case where an LED is used and the half bandwidth is large, it is preferable to reduce the half bandwidth by using a member for limiting the wavelength range, such as a band-pass filter. Further alternatively, the light source may include a lens so that excitation light is emitted onto the measurement object 20 through the lens. Further alternatively, the light source may be disposed at a position away from the measurement object 20, and excitation light may be guided through an optical fiber or a like member to emit excitation light onto the measurement object 20 through the lens. In the above modification, since a detection probe i.e. the image pickup device 50 does not include a light source, the size of the detection probe can be reduced, thereby enhancing the operability of the detection probe. Further alternatively, a xenon lamp or a like member may be used as the excitation light emitter 1. In this modification, in the similar manner as described above, light is guided through an optical fiber, and a filter for limiting the wavelength range is attached to a light incident port or a light exit port of the optical fiber. This enables to reduce the filter size, and also enables to arrange a charging circuit and an emitting circuit required for operating the xenon lamp, as an external element, as well as the xenon lamp. This arrangement enables to reduce the size of the detection probe.

Preferably, the excitation light emitter 1 is operable to change the emission amount of excitation light. For instance, in the case where an LED is used as the excitation light emitter 1, an output from the excitation light emitter 1 can be changed by using an LED capable of changing a current. Further alternatively, providing an arrangement capable of changing the aperture diameter of a light diaphragm, or providing an ND (Neutral Density) filter enables to change the light amount of the LED.

The illumination light emitter 2 may be a light source e.g. a white color LED, or an RGB LED, or a lamp. It is preferable to use a color image, because fluorescence in a color image is easily recognizable. However, a monochromatic image may be usable, and a monochromatic LED may be used as the light source. Further alternatively, the illumination light emitter 2 may be a light source including a lens so that illumination light can be emitted onto the measurement object 20 through the lens. Further alternatively, the light source may be disposed at a position away from the measurement object 20, and illumination light may be guided through an optical fiber or a like member to emit the illumination light onto the measurement object 20 through the lens.

The illumination light emitter 2 is operable to change the emission amount of illumination light. For instance, the output from the illumination light emitter 2 may be changed by using an LED capable of changing a current. Further alternatively, providing an arrangement capable of changing the aperture diameter of a light diaphragm, or providing an ND (Neutral Density) filter enables to change the light amount of the LED.

The image pickup device 50 includes an image sensor 3, a light receiving lens 4 for forming an image of light from the measurement object 20 on the image sensor 3, and an optical filter 5, serving as an excitation light blocker for blocking excitation light. The image pickup device 50 is a camera including the image sensor 3 such as a CCD (Charge Coupled Device) image sensor or a CMOS (Complementary Metal Oxide Semiconductor) image sensor, a diaphragm for adjusting the amount of light to be incident onto the image sensor 3, and the light receiving lens 4. The image pickup device 50 is adapted to sense light from the measurement object 20.

More specifically, the excitation light emitter 1 is operable to emit excitation light onto the measurement object 20, and the illumination light emitter 2 is operable to emit illumination light onto the measurement object 20. The image pickup device 50 is operable to sense light such as fluorescence and reflection light from the measurement object 20 irradiated with excitation light/illumination light. Preferably, the image pickup device 50 has a sensitivity capable of detecting weak fluorescence. In this embodiment, the image pickup device 50 may be a color camera or a monochromatic camera. Preferably, the image pickup device 50 is a color camera, because it is easy to recognize fluorescence in a color image.

The light receiving lens 4 is disposed on the light receiving side of the image sensor 3. An image of light from the measurement object 20 is formed on the image sensor 3 through the light receiving lens 4. Alternatively, the image sensor 3 may be disposed at a position away from the light receiving lens 4, and light from the measurement object 20 may be guided to the image sensor 3 through an imaging fiber.

The optical filter 5 is disposed on the side of the measurement object 20 with respect to the light receiving lens 4. Light from the measurement object 20 is transmitted through the optical filter 5, and an image of the light is formed on the image sensor 3 through the light receiving lens 4. The optical filter 5 has a characteristic of blocking light of a wavelength band identical to the wavelength band of excitation light. In other words, the optical filter 5 does not transmit excitation light. The optical filter 5 may be arranged at a position other than the above.

Figure 2:
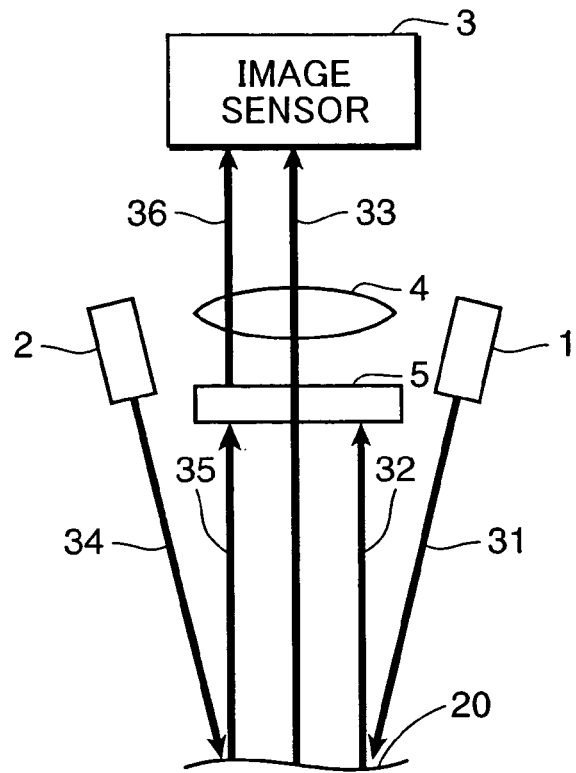
FIG. 2 is a diagram for describing propagating directions of light beams.
Figure 3:
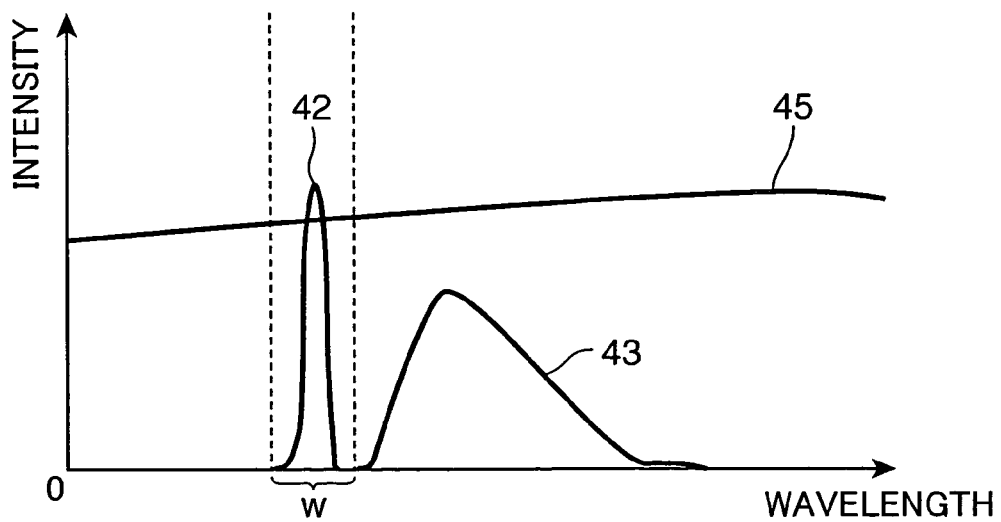
FIG. 3 is a characteristic diagram for describing a relation between characteristics of the light beams, and a characteristic of an optical filter.

In the following, a characteristic of the optical filter 5 is described referring to FIGS. 2 and 3. FIG. 2 is a diagram for describing propagating directions of light beams. FIG. 3 is a characteristic diagram for describing a relation between characteristics of the light beams, and a characteristic of an optical filter. In FIG. 2, a part of the fluorescence detecting apparatus 100 is illustrated, with propagating directions of the light beams. Referring to FIG. 2, an excitation light beam 31 from the excitation light emitter 1 is emitted onto the measurement object 20. In the case where the excitation light beam 31 is emitted onto a fluorescent material contained in the measurement object 20, fluorescence is emitted from the fluorescent material. In this case, light from the measurement object 20 irradiated with the excitation light beam 31 is constituted of an excitation light beam 32 reflected on the measurement object 20, and a fluorescent beam 33. An illumination beam 34 from the illumination light emitter 2 is emitted onto the measurement object 20. In this case, light from the measurement object 20 is constituted of an illumination beam 35 reflected on the measurement object 20. In other words, the light from the measurement object 20 includes the excitation light beam 32 reflected on the measurement object 20, the fluorescent beam 33, and the illumination light beam 35 reflected on the measurement object 20. These light beams 32, 33, and 35 are incident onto the optical filter 5 having a characteristic of blocking light of a wavelength band identical to the wavelength band of excitation light.

The above arrangement is described referring to FIG. 3. In FIG. 3, the horizontal axis indicates a wavelength of light, and the vertical axis indicates an intensity of light. FIG. 3 shows a wavelength characteristic curve 42 of the excitation light beam 32, a wavelength characteristic curve 43 of the fluorescent beam 33, and a wavelength characteristic curve 45 of the illumination light beam 35. Since the fluorescent beam 33 has a low intensity, the wavelength characteristic curve 43 of the fluorescent beam 33 is shown, with the magnitude thereof in the vertical axis being increased, as compared with the wavelength characteristic curve 42 and the wavelength characteristic curve 45.

The optical filter 5 has a notch characteristic of blocking light of a cutoff wavelength band "w". Specifically, the cutoff wavelength band "w" is a wavelength range capable of blocking all the excitation light reflected on the measurement object 20. The entirety of the wavelength characteristic curve 42 is included in the cutoff wavelength band "w", and the wavelength band of the wavelength characteristic curve 42 is narrow. The wavelength characteristic curve 43 has a low intensity, and only a small part of the wavelength characteristic curve 43 is included in the cutoff wavelength band "w". In this example, the light source of the illumination light emitter 2 is a white color lamp having no wavelength dependency. The wavelength characteristic curve 45 represents a wavelength characteristic of reflection light, in the case where the measurement object 20 has a white color. In this example, the wavelength characteristic curve 45 has a substantially uniform intensity, and shows a wide wavelength band. If the measurement object 20 has a specific color, a wavelength characteristic corresponding to the color is obtained.

Referring to FIG. 3, light corresponding to the cutoff wavelength band "w" is blocked. In this example, the entirety of the wavelength characteristic curve 42 of the excitation light beam 32 reflected on the measurement object 20 is included in the cutoff wavelength band "w". A part of the wavelength characteristic curve 45 of the illumination light beam 35 reflected on the measurement object 20 is also included in the cutoff wavelength band "w". Accordingly, there is no likelihood that the excitation light beam 32 reflected on the measurement object 20 may be transmitted through the optical filter 5. Although a part of the illumination light beam 35 reflected on the measurement object 20 is cut off by the optical filter 5, a primary part of the illumination light beam 35 is transmitted through the optical filter 5. As described above, only a small part of the fluorescent beam 33 is included in the cutoff wavelength band "w", and a primary part of the fluorescent beam 33 is transmitted through the optical filter 5. In other words, the fluorescent beam 33, and an illumination light beam 36, which is obtained by transmitting the illumination light beam 35 through the optical filter 5, form an image on the image sensor 3. Hereinafter, an image defined by fluorescence is called as a "fluorescent image", and an entire image of a measurement object defined by the illumination light beam 36 is called as a "measurement object image". Defining the cutoff wavelength band "w" of the optical filter 5 as described above enables to avoid a likelihood that the excitation light beam 32 reflected on the measurement object 20 may be sensed by the image sensor 3. The above arrangement enables to obtain a desirable image, while eliminating an influence of the excitation light beam 32 reflected on the measurement object 20 to an image to be formed on the image sensor 3.

In the case where the width of the cutoff wavelength band "w" is large, a part of the illumination light beam 36 reflected on the measurement object 20 is likely to be missing, and the color reproducibility may be lowered. It is preferable to reduce the width of the cutoff wavelength band "w" as much as possible to obtain a desirable image having superior color reproducibility. In view of this, it is preferable to reduce the width of the half bandwidth of the excitation light beam 31. This enables to reduce the width of the cutoff wavelength band "w" of the optical filter 5. Preferably, the cutoff wavelength band "w" does not include the wavelength band of the fluorescent beam 33. The above arrangement enables to obtain a desirable image, without a likelihood that the intensity of the fluorescent beam 33 may be lowered by an optical filter.

The personal computer 6 includes the controller 8 and the storage 9. The controller 8 is operable to control the excitation light emitter 1, the illumination light emitter 2, and the image pickup device 50. Specifically, the controller 8 is operable to control an emission timing of the excitation light emitter 1, an emission timing of the illumination light emitter 2, a light amount of the excitation light emitter 1, a light amount of the illumination light emitter 2, an image pickup condition and an image pickup timing of the image pickup device 50, and the like. The image pickup condition is a condition to be defined with respect to the image pickup device 50. Examples of the image pickup condition include a shutter speed, an aperture, a gain, an optical magnification ratio i.e. an F-number which is varied depending on a zoom operation.

The storage 9 stores, in advance, light amounts of illumination light, each of which is optimally set depending on an image pickup condition and a brightness level. The light amounts of illumination light corresponding to the image pickup conditions may be stored in the storage 9 at the time of e.g. producing the fluorescence detecting apparatus 100. Further alternatively, a value of light amount which is estimated to be optimal by the operator may be stored in the storage 9, each time the fluorescence detecting apparatus 100 is used.

The display section 7 is connected to the personal computer 6. The display section 7 is operable to display an image obtained by the image pickup device 50 under the control of the controller 8. The operator is allowed to specify the position of the fluorescent material with respect to the measurement object 20, based on an image displayed on the display section 7.

Operation of Embodiment

In this Section, an Operation of the Embodiment is Described.

Figure 4:
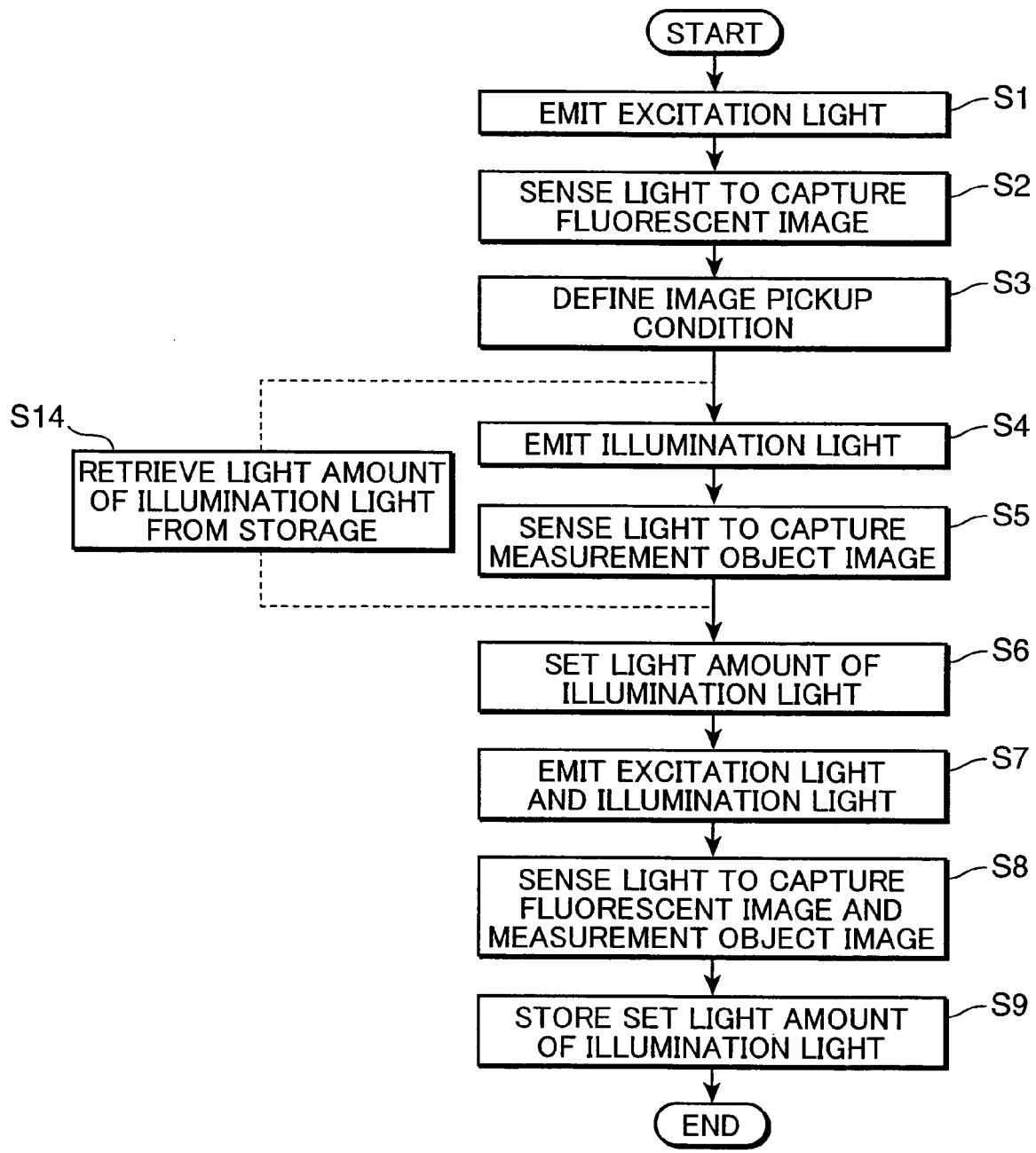
FIG. 4 is a flowchart for describing an operation to be performed by the fluorescence detecting apparatus of the embodiment.
Figure 5:
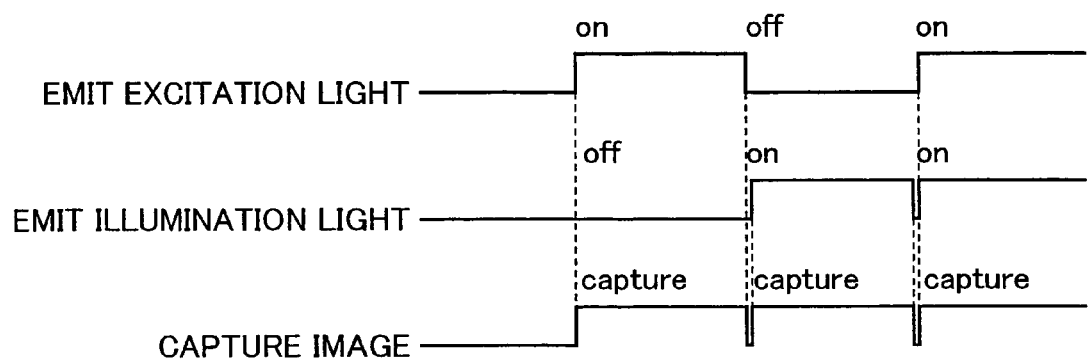
FIG. 5 is a timing chart on emission operations and image pickup operations to be performed by the fluorescence detecting apparatus of the embodiment.

FIG. 4 is a flowchart for describing an operation to be performed by the fluorescence detecting apparatus of the embodiment. FIG. 5 is a timing chart on emission operations and image pickup operations to be performed by the fluorescence detecting apparatus of the embodiment.

Control operations to be performed by the controller 8 are described referring to FIG. 4, as well as FIG. 1. First, the controller 8 causes the excitation light emitter 1 to emit the excitation light beam 31 onto the measurement object 20 (Step S1). Then, the controller 8 causes the image pickup device 50 to sense light from the measurement object 20 irradiated with the excitation light beam 31 (Step S2). In the above condition, the light from the measurement object 20 is constituted of the fluorescent beam 33 to be emitted from the fluorescent material contained in the measurement object 20 irradiated with the excitation light beam 31, and the excitation light beam 32 reflected on the measurement object 20. Since the excitation light beam 32 is not transmitted through the optical filter 5, solely a fluorescent image defined by the fluorescence beam 33 is formed on the image sensor 3 through the light receiving lens 4, whereby the fluorescent image is captured by the image pickup device 50.

The controller 8 defines an image pickup condition to make the brightness of the fluorescent image optimum, based on an image pickup result i.e. the fluorescent image, and sets the image pickup condition in the image pickup device 50 (Step S3). After the image pickup condition is defined, the controller 8 causes the illumination light emitter 2 to emit the illumination light beam 34 onto the measurement object 20, while suspending an operation of emitting the excitation light beam 31 from the excitation light emitter 1 (Step S4). Then, the controller 8 causes the image pickup device 50 to sense light from the measurement object 20 irradiated with the illumination light beam 34 (Step S5). In this condition, the light from the measurement object 20 is constituted of the illumination light beam 35 reflected on the measurement object 20. Since the optical filter 5 is operable to block light of a wavelength band identical to the wavelength band of excitation light, an image defined by the illumination light beam 36, devoid of the light of the wavelength band identical to the wavelength band of excitation light, is formed on the image sensor 3 through the light receiving lens 4. Thereby, a measurement object image is captured.

The controller 8 determines a light amount of illumination light to be emitted from the illumination light emitter 2 which makes the brightness of the measurement object image optimum, based on the measurement object image; and sets the light amount in the illumination light emitter 2 (Step S6). In setting the light amount of illumination light, a brightness level i.e. a targeted pixel output value may also be set. In other words, the operator is allowed to change the brightness level by manipulating the brightness level setter 11. In the case where the operator does not designate a brightness level, a predetermined brightness level may be used. An example of the predetermined brightness level is defined in such a manner that the pixel output of a measurement object image is 10% with respect to a saturated pixel output of the image sensor 3. The light amount of illumination light to be emitted from the illumination light emitter 2 in Step S4 may also be defined based on the predetermined brightness level. In the case where a measurement object image is too bright, it may be impossible or difficult for the operator to distinguish a fluorescent image from the measurement object image. In view of this, it is preferable to set a proper light amount of illumination light so that the operator is enabled to clearly recognize a fluorescent image on the display section 7.

In setting the light amount of illumination light, a light amount of illumination light corresponding to the image pickup condition defined in Step S3 may be retrieved from the storage 9, in which each of the light amounts of illumination light is stored in correlation to an image pickup condition and a brightness level, without executing the operations in Step S4 and Step S5. Specifically, the routine may proceed from Step S3 to Step S14, where a light amount of illumination light corresponding to the image pickup condition defined in Step S3, and the predetermined brightness level is retrieved from the storage 9. Then, the retrieved light amount of illumination light may be set in the illumination light emitter 2 (Step S6).

By performing the above operations, an image pickup condition and a light amount of illumination light optimum for detecting the position of the fluorescent material with respect to the measurement object 20 are determined and set. Then, the controller 8 causes the excitation light emitter 1 and the illumination light emitter 2 to simultaneously emit the excitation light beam 31 and the illumination light beam 34 onto the measurement object 20, respectively (Step S7). Then, the fluorescent beam 33 and the illumination light beam 36 out of the light from measurement object 20 irradiated with the excitation light beam 31 and the illumination light beam 34 are sensed by the image pickup device 50 to capture a fluorescent image and a measurement object image (Step S8). Since the image pickup condition and the light amount of illumination light are set in the respective optimum conditions, the fluorescent image and the measurement object image captured by the image pickup device 50 are displayed in a desirable state. Accordingly, the operator is allowed to accurately specify the fluorescent portion with respect to the measurement object 20. Thus, the operator is allowed to accurately specify the position of the fluorescent material with respect to the measurement object 20.

Since a fluorescent image and a measurement object image are simultaneously captured by simultaneously emitting excitation light and illumination light, the position of the fluorescent material can be accurately specified without positional displacement of the fluorescent image with respect to the measurement object image, even if the measurement object 20 is moved during an image pickup operation. In the above arrangement, there is no need of individually providing an image pickup device for capturing a fluorescent image, and an image pickup device for capturing a measurement object image. This is advantageous in reducing the size and the cost of the fluorescence detecting apparatus.

After the fluorescent image and the measurement object image are captured by the image pickup device 50 (Step S8), the controller 8 causes the storage 9 to store the light amount of illumination light set in the current image pickup operation in correlation to the image pickup condition and the brightness level (Step S9). In the case where Step S9 is executed, if it is judged that the image pickup condition defined by the controller 8 is improper for some reason, the operator may adjust the light amount of illumination light to set a proper image pickup condition, and an image pickup operation may be performed in response to the operator's manipulating an operation member (not shown). Alternatively, after the operator adjusts the light amount of illumination light, the controller 8 may automatically causes the storage 9 to store the adjusted light amount of illumination light. The above modification enables to utilize a light amount of illumination light optimum for an image pickup condition obtained by a current image pickup operation, thereby enabling to acquire a proper image.

The timings on an emission operation of the excitation light emitter 1, an emission operation of the illumination light emitter 2, and an image pickup operation of the image sensor 3 to be performed in the operation of the fluorescence detecting apparatus 100 of the embodiment are illustrated in FIG. 5.

Figure 6A:
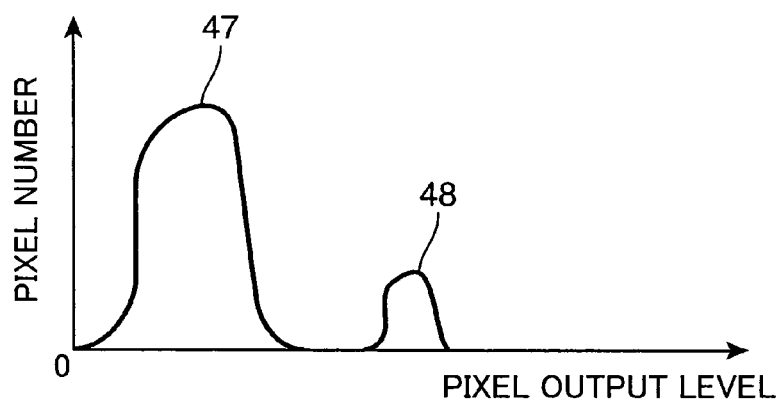
FIG. 6A is a diagram showing an example of a histogram in the case where a desirable image is obtained.
Figure 6B:
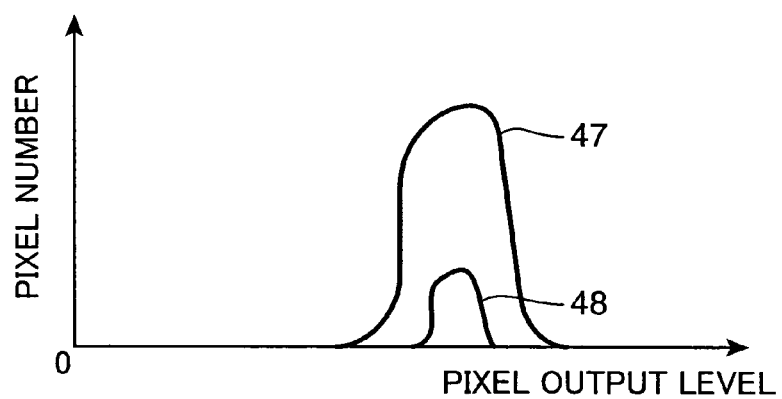
FIG. 6B is a diagram showing an example of a histogram in the case where a desirable image is not obtained.

A fluorescent image and a measurement object image to be obtained by image pickup operations of the image pickup device 50 in the fluorescence detecting apparatus 100 are described referring to a histogram. FIG. 6A is a diagram showing an example of a histogram in the case where a desirable image is obtained. FIG. 6B is a diagram showing an example of a histogram in the case where a desirable image is not obtained.

Referring to FIGS. 6A and 6B, the horizontal axis indicates a pixel output level, and the vertical axis indicates the pixel number. A measurement object image defined by the illumination light beam 36, and a fluorescent image defined by the fluorescent beam 33 are different from each other in brightness. An image characteristic curve 47 of a measurement object image, and an image characteristic curve 48 of a fluorescent image are shown in FIGS. 6A and 6B.

As shown in FIG. 6A, in a state that the image characteristic curve 47 of a measurement object image, and the image characteristic curve 48 of a fluorescent image are greatly different from each other in the pixel output level, a measurement object image and a fluorescent image are displayed on the display section 7 in a desirable state where the fluorescent image is clearly distinguished from the measurement object image. Thereby, the position of the fluorescent material with respect to the measurement object 20 can be specified.

On the other hand, for instance, in the case where the image characteristic curve 47 of a measurement object image, and the image characteristic curve 48 of a fluorescent image are close to each other in the pixel output level, as shown in FIG. 6B, the image characteristic curve 47 of a measurement object image, and the image characteristic curve 48 of a fluorescent image are overlapped with each other. Specifically, the image characteristic curve 48 of a fluorescent image is included in the image characteristic curve 47 of a measurement object image. This state indicates that a fluorescent image is less or not distinguished from a measurement object image.

The fluorescence detecting apparatus 100 of the embodiment is constructed in such a manner that an image pickup condition and a light amount of illumination light are optimally set, while avoiding a condition that a histogram image as shown in e.g. FIG. 6B is obtained; and excitation light and illumination light are simultaneously emitted onto the measurement object 20 to simultaneously capture a fluorescent image and a measurement object image. This arrangement enables to obtain a histogram image, as shown in FIG. 6A, where a fluorescent image and a measurement object image are distinguished from each other.

The above description is made based on the premise that an image pickup condition and a light amount of illumination light are automatically set. As described above, the fluorescence detecting apparatus 100 of the embodiment includes the image pickup condition setter 10, the brightness level setter 11, and the excitation light amount setter 12 so that the operator is allowed to manually set an image pickup condition or a like parameter to an intended value.

In the following, an operation to be performed by the fluorescence detecting apparatus 100 of the embodiment is described, in the case where the image pickup condition setter 10, the brightness level setter 11, and the excitation light amount setter 12 are operated.

First, a method for manipulating the image pickup condition setter 10 is described. In the case where excitation light and illumination light are simultaneously emitted onto the measurement object 20 to perform an image pickup operation, there is a case that a fluorescent image is not observed due to a low intensity of fluorescence. In this occasion, the operator is allowed to change the image pickup condition to an intended image pickup condition by manipulating the image pickup condition setter 10.

Specifically, in response to setting an intended image pickup condition by the operator's manipulating the image pickup condition setter 10, the controller 8 causes the image pickup device 50 to perform an image pickup operation in the set image pickup condition. For instance, in the case where the operator wishes to perform an image pickup operation with a slow shutter speed to increase the detection sensitivity of fluorescence, the shutter speed can be reduced by the operator manipulating the image pickup condition setter 10. In this example, the shutter speed corresponds to a charge accumulation period of a CCD image sensor. In the case where the light receiving lens 4 is a zoom lens, it is possible to change the optical magnification ratio so as to vary the measurement area by the operator manipulating the image pickup condition setter 10. Thereby, the brightness of the light receiving lens 4 i.e. the F-number is changed.

In the case where the image pickup condition is changed as described above, preferably, the routine may proceed to Step S4 in FIG. 4, where the light amount of illumination light corresponding to the changed image pickup condition is set. By setting the light amount of illumination light in Step S4 as described above, a light amount of illumination light optimum for the image pickup condition is set. Further alternatively, the routine may proceed to Step S14, in place of proceeding to Step S4, a light amount of illumination light optimum for the image pickup condition may be selected from the light amounts of illumination light stored in the storage 9 (Step S14), and the selected light amount of illumination light may be set in the illumination light emitter 2 (Step S6).

The image pickup condition may be changed after the image pickup condition is defined in Step S3 in FIG. 4, in place of after the step of obtaining a fluorescent image and a measurement object image. Specifically, after an image pickup condition is defined, a fluorescent image obtained by emitting excitation light onto the measurement object 20 in the image pickup condition is displayed on the display section 7. In the case where a desirable image is not displayed on the display section 7, because of weak fluorescence or a like factor, the operator may change the image pickup condition to an intended image pickup condition. In the case where a desirable image is not obtained by a one-time image pickup operation, an intended image may be obtained by performing the above operation multiple number of times.

In the following, a method for manipulating the brightness level setter 11 is described. The brightness level to be set by the brightness level setter 11 corresponds to a targeted pixel output value. Specifically, the brightness level corresponds to a targeted value of pixel output level of a measurement object image with respect to e.g. a saturated pixel output of the image sensor 3 to be obtained by emitting illumination light. The controller 8 is operable to set a light amount of illumination light so that the light amount of illumination light to be emitted from the illumination light emitter 2 corresponds to the set brightness level. It is preferable to set the brightness of a measurement object image to be obtained by emission of the illumination light beam 36 to a moderately small value to make a fluorescent image clearly distinguished from a measurement object image. Specifically, it is preferable to set the pixel output of the measurement object image to e.g. about 0 to 10% with respect to the saturated pixel output of the image sensor 3, considering an average output from all the pixels of the image sensor 3. Manipulating the brightness level setter 11 by the operator enables to designate a targeted pixel output value of the measurement object image to be defined by the illumination light beam 36. The brightness level may be defined by referring to a maximum value of pixel output out of all the pixel outputs, or may be set to an average value of pixel output with respect to a specific area of the measurement object 20 e.g. a central area of the measurement object 20.

For instance, the operator may judge whether setting the brightness level is necessary, based on an obtained image. If it is judged that setting the brightness level is necessary, the operator designates an intended value. Thereby, the controller 8 is operable to define an optimum light amount of illumination light to attain an intended brightness level. Preferably, in response to setting the brightness level by the operator's manipulating the brightness level setter 11, the routine may proceed to Step S4 in FIG. 4, where an optimum light amount of illumination light is set, based on a measurement object image to be obtained by emitting the illumination light beam 34 of the changed light amount onto the measurement object 20. By performing the above operation, the light amount of illumination light corresponding to the intended brightness level is set. Further alternatively, the routine may proceed to Step S14, in place of proceeding to Step S4, an optimum light amount of illumination light corresponding to a set brightness level may be retrieved from the storage 9 (Step S14), and the retrieved light amount of illumination light may be set (Step S6). In the case where the brightness level i.e. the aforementioned pixel output level with respect to the saturated pixel output is set to 0%, an operation of emitting illumination light is suspended.

The brightness level may be set after the light amount of illumination light is set in Step S6 in FIG. 4. Specifically, after the light amount of illumination light is set, a measurement object image is obtained by emitting illumination light of the set light amount onto the measurement object 20, and the measurement object image is displayed on the display section 7. In the case where a desirable image is not obtained e.g. the measurement object image displayed on the display section 7 is too bright, i.e. the light amount of illumination light is unduly large, the operator may adjust the brightness level by manipulating the brightness level setter 11. In the case where a desirable image is not obtained by a one-time image pickup operation, a desirable image can be obtained by performing the above operations multiple number of times.

Next, a method for manipulating the excitation light amount setter 12 is described. With use of the excitation light amount setter 12, the operator is allowed to change the light amount of excitation light to be emitted from the excitation light emitter 1 to an intended value. In the case where the operator judges that the light amount of excitation light is unduly small, the operator is allowed to set the light amount of excitation light to an intended value by manipulating the excitation light amount setter 12. Specifically, in response to designating the light amount of excitation light to an intended value by the operator's manipulating the excitation light amount setter 12, the controller 8 causes the excitation light amount setter 12 so that the light amount of excitation light to be emitted from the excitation light emitter 1 corresponds to the intended value. Thereby, a desirable image can be obtained. Further alternatively, the light amount of excitation light may be increased so that a fluorescent image is clearly distinguished from a measurement object image.

Figure 7:
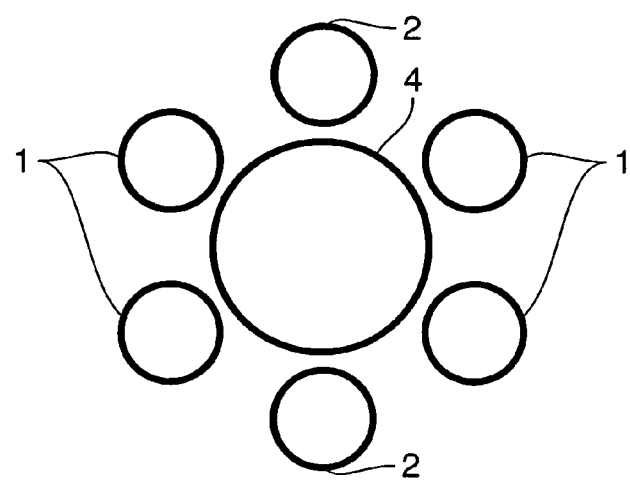
FIG. 7 is a diagram showing an arranged position of excitation light emitters, illumination light emitters, and a light receiving lens in the fluorescence detecting apparatus of the embodiment.

In the following, an example of an arranged position of the excitation light emitter, the illumination light emitter, and the light receiving lens in the fluorescence detecting apparatus of the embodiment is described. In this example, the fluorescence detecting apparatus includes four excitation light emitters 1, two illumination light emitters 2, and one light receiving lens 4. FIG. 7 is a diagram showing an arranged position of the excitation light emitters 1, the illumination light emitters 2, and the light receiving lens 4 in the fluorescence detecting apparatus 100 of the embodiment. FIG. 7 is a diagram, wherein the excitation light emitters 1, the illumination light emitters 2, and the light receiving lens 4 are viewed in a direction of an optical axis of the light receiving lens 4. The excitation light emitters 1, the illumination light emitters 2, and the light receiving lens 4 may be arranged in the respective positions as shown in e.g. FIG. 7. Specifically, the excitation light emitters 1 and the illumination light emitters 2 are arranged around the light receiving lens 4. Generally, an intensity of fluorescence is small, as compared with an intensity of illumination light. Accordingly, it is preferable to set the number of the excitation light emitters 1 larger than the number of the illumination light emitters 2 to display a fluorescent image and a measurement object image as clearly distinguished from each other.

Figure 8:
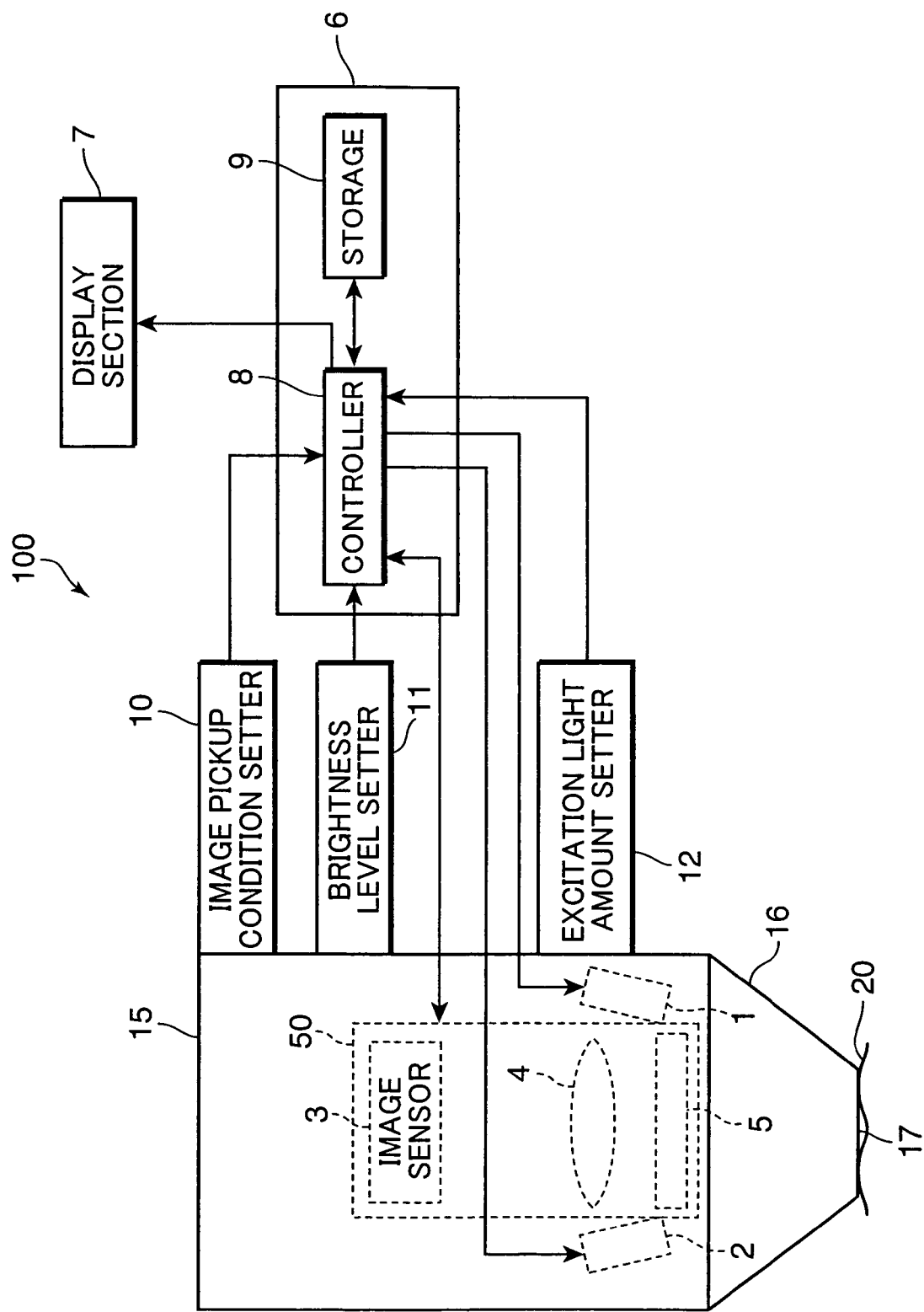
FIG. 8 is a diagram showing an arrangement of a fluorescence detecting apparatus as a modification of the embodiment, wherein the fluorescence detecting apparatus is provided with a hood portion.

Next, a modified embodiment of the fluorescence detecting apparatus is described, wherein the fluorescence detecting apparatus is provided with a hood portion. FIG. 8 is a diagram showing an arrangement of a fluorescence detecting apparatus provided with a hood portion. As shown in FIG. 8, the fluorescence detecting apparatus 100 may include the hood portion.

For instance, an excitation light emitter 1, an illumination light emitter 2, and an image pickup device 50 are provided in the interior of an apparatus body 15, as a measurement probe; and an image pickup condition setter 10, a brightness level setter 11, and an excitation light amount setter 12 are provided on the exterior of the apparatus body 15. The apparatus body 15 may provided with a hood portion 16 having an opening 17, and the hood portion 16 covers a region from a measurement portion of the measurement object 20 to the apparatus body 15 is provided. It is necessary to set the dimensions of the opening 17 in the hood portion 16 larger than the dimensions of the measurement portion of the measurement object 20.

The hood portion 16 has a tapered shape toward the opening 17 corresponding to a distal end of the hood portion 16 to guide light onto the measurement object 20. Preferably, a light receiving lens 4 is disposed at such a position that an image of light from the measurement object 20 is formed on an image sensor 3, in the case where the opening 17 or its vicinity is contacted with or in proximity to the measurement object 20. In use of the fluorescence detecting apparatus 100, the operator holds the apparatus body 15, and contacts the opening 17 or its vicinity with or in proximity to the measurement object 20, while directing the opening 17 toward the measurement portion of the measurement object 20. This enables to eliminate a focus adjusting operation.

The fluorescence detecting apparatus 100 has a feature that the region from the measurement portion of the measurement object 20 to the apparatus body 15 is covered by the hood portion 16. This arrangement enables to eliminate a likelihood that external light may be incident onto a measurement portion, thereby enabling to obtain an image without an influence of external light.

With use of the fluorescence detecting apparatus of the embodiment, weak fluorescence to be emitted from a fluorescent material for labeling cancerous cells can be visually observed. Examples of the fluorescent material to be impregnated into a living body include fluorescent beads e.g. Fluoresbrite™ (Polysciences) and Estapor® (Merck Chime, S.A.S); and quantum dots e.g. Qdot® (Invitrogen) and Qtracker™ (Quantum Dot Corporation), in addition to various fluorescent pigments. TelomeScan® (OBP401 of Oncolys BioPharma Inc.), as a fluorescent virus, is designed in such a manner that the virus is proliferated in cancerous cells when impregnated in a living body, GFP (green fluorescent protein) is produced in the cells, and fluorescence is emitted. With use of the fluorescence detecting apparatus of the embodiment, the position of cancerous cells can be accurately specified by observing weak fluorescence to be emitted from a fluorescent virus.

The specification discloses the aforementioned various arrangements. The following is a summary of the embodiment.

A novel fluorescence detecting apparatus includes: an excitation light emitter for emitting excitation light exciting a fluorescent material onto a measurement object; an illumination light emitter for emitting illumination light onto the measurement object; an image pickup device for sensing light from the measurement object; and a controller for controlling the image pickup device, the excitation light emitter, and the illumination light emitter, wherein the controller is operable to cause the excitation light emitter to emit the excitation light onto the measurement object to define an image pickup condition of the image pickup device, based on an image pickup result to be obtained by sensing light from the measurement object irradiated with the excitation light by the image pickup device, the controller is operable to set a light amount of the illumination light to be emitted from the illumination light emitter depending on the image pickup condition, and the controller is operable to cause the excitation light emitter and the illumination light emitter to simultaneously emit the excitation light, and the illumination light of the set light amount, to cause the image pickup device to sense light from the measurement object irradiated with the excitation light and the illumination light.

In the above arrangement, the entirety of the measurement object and the fluorescent portion can be sensed in an optimum image pickup condition and with an optimum light amount of illumination light. This enables to acquire a desirable image. Also, since a fluorescent image and a measurement object image can be simultaneously captured, an image can be acquired without positional displacement of the fluorescent image with respect to the measurement object image, even if the measurement object is moved during an image pickup operation. Thereby, the position of the fluorescent material with respect to the measurement object can be accurately specified. Also, since the above arrangement can be realized by a single image pickup device, the size and the cost of the fluorescence detecting apparatus can be reduced.

In the fluorescence detecting apparatus, preferably, the controller may be operable to cause the illumination light emitter to emit the illumination light so as to set the light amount of the illumination light, based on an image pickup result to be obtained by sensing light from the measurement object irradiated with the illumination light by the image pickup device, after the image pickup condition is defined.

The above arrangement enables to obtain an optimum light amount of illumination light.

Preferably, the fluorescence detecting apparatus may further include a storage for storing in advance the light amount of the illumination light corresponding to the image pickup condition, wherein the controller is operable to retrieve the light amount of the illumination light corresponding to the defined image pickup condition from the storage, and set the retrieved light amount of the illumination light.

The above arrangement enables to obtain an optimum light amount of illumination light.

Preferably, the fluorescence detecting apparatus may further include an image pickup condition setter for changing the image pickup condition, wherein the controller is operable to control the image pickup device in such a manner that the image pickup condition of the image pickup device coincides with the image pickup condition set by the image pickup condition setter.

In the above arrangement, in the case where the operator wishes to change the image pickup condition set in the fluorescence detecting apparatus, the operator is allowed to change the image pickup condition to an intended image pickup condition. For instance, in the case the intensity of a fluorescent image is too small for the operator to recognize, the operator is allowed to set an intended image pickup condition. Further, there is a case that the operator wishes to manually change the image pickup condition. For instance, there is a case that the operator wishes to check whether there is fluorescence of a low intensity which is not displayed as a fluorescent image due to a bright image of the measurement object. Specifically, there is a case that a measurement object includes a fluorescent portion of a high intensity and a fluorescent portion of a low intensity, and the operator wishes to check whether there is a fluorescent portion of a low intensity which is not displayed as a fluorescent image, although the fluorescent portion of a high intensity is captured as a fluorescent image, with a substantially proper light amount of illumination light for observation. Further, there is a case that the light amount of illumination light for observation is not proper, and even a fluorescent portion of a high intensity cannot be displayed as a fluorescent image. In the above conditions, the operator is allowed to check whether a fluorescent material resides in the measurement object by e.g. performing an image pickup condition with a reduced shutter speed, with use of the image pickup condition setter.

Preferably, the fluorescence detecting apparatus may further include a brightness level setter for setting a targeted value of a pixel output, wherein the controller is operable to set the light amount of the illumination light in such a manner that the light amount of the illumination light to be emitted from the illumination light emitter corresponds to the targeted value of the pixel output set by the brightness level setter.

In the above arrangement, the operator is allowed to set the brightness level i.e. the targeted pixel output value in such a manner that the light amount of the illumination light to be emitted from the illumination light emitter corresponds to the brightness level. This enables to obtain an optimum light amount of illumination light. In the specification, a targeted pixel output value corresponds to a pixel output level of a measurement object image with respect to e.g. a saturated pixel output of an image sensor.

Preferably, the fluorescence detecting apparatus may further include an excitation light amount setter for changing a light amount of the excitation light to be emitted from the excitation light emitter, wherein the controller is operable to set the light amount of the excitation light in such a manner that the light amount of the excitation light to be emitted from the excitation light emitter coincides with the light amount of the excitation light set by the excitation light amount setter.

In the above arrangement, the operator is allowed to change the light amount of excitation light to an intended light amount.

Preferably, the fluorescence detecting apparatus may further include a hood portion having an opening with dimensions larger than dimensions of a measurement portion of the measurement object.

The above arrangement enables to obtain a desirable image without an influence of external light. Also, the above arrangement eliminates the need of a focus adjusting operation by the operator, by disposing a light receiving lens at such a position that an image of light from the measurement object is formed on an image sensor in a state that the opening or its vicinity is contacted with or in proximity to the measurement object.

A novel fluorescence detecting method includes the steps of: defining an image pickup condition based on an image pickup result to be obtained by sensing fluorescence to be emitted from a measurement object irradiated with excitation light exciting a fluorescent material; setting a light amount of illumination light based on the image pickup condition; and emitting the excitation light and the illumination light onto the measurement object to sense light from the measurement object irradiated with the excitation light and the illumination light, whereby a position of the fluorescent material with respect to the measurement object is detected.

In the above arrangement, the entirety of the measurement object and the fluorescent portion can be sensed in an optimum image pickup condition and with an optimum light amount of illumination light. This enables to acquire a desirable image. Thereby, the position of the fluorescent material with respect to the measurement object can be accurately detected based on an image. Also, since a fluorescent image and a measurement object image can be simultaneously captured, an image can be acquired without positional displacement of the fluorescent image with respect to the measurement object image, even if the measurement object is moved during an image pickup operation.

In the fluorescence detecting method, preferably, after the image pickup condition defining step, the light amount of the illumination light may be set based on an image pickup result to be obtained by sensing light from the measurement object irradiated with the illumination light.

The above arrangement enables to obtain an optimum light amount of illumination light.

In the fluorescence detecting method, preferably, the light amount of the illumination light corresponding to the image pickup condition may be stored in advance, and after the image pickup condition defining step, the light amount of the illumination light corresponding to the image pickup condition defined in the image pickup condition defining step may be set.

The above arrangement enables to obtain an optimum light amount of illumination light.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A fluorescence detecting apparatus comprising:
   an excitation light emitter for emitting: a first excitation light for exciting a fluorescent material within a measurement object to define an exposure condition and a second excitation light for exciting the fluorescent material within the measurement object;
   an illumination light emitter for emitting first illumination light onto the measurement object;
   an image pickup device for sensing light from the measurement object; and
   a controller for controlling the image pickup device, the excitation light emitter, and the illumination light emitter, wherein the controller is operable to:
   cause the excitation light emitter to emit the first excitation light within the measurement object to define an exposure condition of the image pickup device, based on an image pickup result to be obtained by sensing light from the measurement object irradiated with the first excitation light by the image pickup device, so that a fluorescent portion of the measurement object excited by the second excitation light has a proper exposure in the exposure condition,
   set a light amount of the first illumination light to be emitted from the illumination light emitter depending on the exposure condition so that the measurement object illuminated by the illumination light has a proper exposure in the exposure condition, and cause the excitation light emitter and the illumination light emitter to simultaneously emit the second excitation light, and the first illumination light of the set light amount, to cause the image pickup device to sense light from the measurement object irradiated with the second excitation light and the first illumination light.

2. The fluorescence detecting apparatus according to claim 1, wherein the controller is operable to cause the illumination light emitter to emit second illumination light so as to set the light amount of the first illumination light, based on an image pickup result to be obtained by sensing light from the measurement object irradiated with the second illumination light by the image pickup device, after the exposure condition is defined.

3. The fluorescence detecting apparatus according to claim 2, further comprising: an image pickup condition setter for changing the exposure condition, wherein the controller is operable to control the image pickup device in such a manner that the exposure condition of the image pickup device coincides with the exposure condition set by the image pickup condition setter.

4. The fluorescence detecting apparatus according to claim 2, further comprising: a brightness level setter for setting a targeted value of a pixel output, wherein the controller is operable to set the light amount of the first illumination light in such a manner that the light amount of the first illumination light to be emitted from the illumination light emitter corresponds to the targeted value of the pixel output set by the brightness level setter.

5. The fluorescence detecting apparatus according to claim 2, further comprising: an excitation light amount setter for changing a light amount of the second excitation light to be emitted from the excitation light emitter, wherein the controller is operable to set the light amount of the second excitation light in such a manner that the light amount of the second excitation light to be emitted from the excitation light emitter coincides with the light amount of the second excitation light set by the excitation light amount setter.

6. The fluorescence detecting apparatus according to claim 2, further comprising: a hood portion having an opening larger than a measurement portion of the measurement object.

7. The fluorescence detecting apparatus according to claim 1, further comprising: a storage for storing in advance the light amount of the first illumination light corresponding to the exposure condition, wherein the controller is operable to retrieve the light amount of the first illumination light corresponding to the defined exposure condition from the storage, and set the retrieved light amount of the first illumination light.

8. The fluorescence detecting apparatus according to claim 7, further comprising: an image pickup condition setter for changing the exposure condition, wherein the controller is operable to control the image pickup device in such a manner that the exposure condition of the image pickup device coincides with the exposure condition set by the image pickup condition setter.

9. The fluorescence detecting apparatus according to claim 7, further comprising: a brightness level setter for setting a targeted value of a pixel output, wherein the controller is operable to set the light amount of the first illumination light in such a manner that the light amount of the first illumination light to be emitted from the illumination light emitter corresponds to the targeted value of the pixel output set by the brightness level setter.

10. The fluorescence detecting apparatus according to claim 7, further comprising: an excitation light amount setter for changing a light amount of the second excitation light to be emitted from the excitation light emitter, wherein the controller is operable to set the light amount of the second excitation light in such a manner that the light amount of the second excitation light to be emitted from the excitation light emitter coincides with the light amount of the second excitation light set by the excitation light amount setter.

11. The fluorescence detecting apparatus according to claim 7, further comprising: a hood portion having an opening larger than a measurement portion of the measurement object.

12. The fluorescence detecting image apparatus according to claim 1, further comprising: an image pickup condition setter for changing the exposure condition, wherein the controller is operable to control the image pickup device in such a manner that the exposure condition of the image pickup device coincides with the exposure condition set by the image pickup condition setter.

13. The fluorescence detecting apparatus according to claim 1, further comprising: a brightness level setter for setting a targeted value of a pixel output, wherein the controller is operable to set the light amount of the first illumination light in such a manner that the light amount of the first illumination light to be emitted from the illumination light emitter corresponds to the targeted value of the pixel output set by the brightness level setter.

14. The fluorescence detecting apparatus according to claim 1, further comprising: an excitation light amount setter for changing a light amount of the second excitation light to be emitted from the excitation light emitter, wherein the controller is operable to set the light amount of the second excitation light in such a manner that the light amount of the second excitation light to be emitted from the excitation light emitter coincides with the light amount of the second excitation light set by the excitation light amount setter.

15. The fluorescence detecting apparatus according to claim 1, further comprising: a hood portion having an opening larger than a measurement portion of the measurement object.

16. A fluorescence detecting method comprising:
defining an exposure condition based on an image pickup result to be obtained by sensing fluorescence to be emitted from a measurement object irradiated with first excitation light exciting a fluorescent material, wherein the exposure condition is such that the fluorescence sensed has a proper exposure in the exposure condition of the image pickup device;
setting a light amount of first illumination light based on the exposure condition so that the measurement object irradiated with second excitation light has a proper exposure in the exposure condition; and
emitting the second excitation light and the first illumination light onto the measurement object to sense light from the measurement object irradiated with the second excitation light and the first illumination light, whereby a position of the fluorescent material with respect to the measurement object is detected.

17. The fluorescence detecting method according to claim 16, wherein after the defining the exposure condition, the light amount of the first illumination light is set based on an image pickup result to be obtained by sensing light from the measurement object irradiated with second illumination light.

18. The fluorescence detecting method according to claim 16, wherein the light amount of the first illumination light corresponding to the exposure condition is stored in advance, and after the defining the exposure condition, setting the light amount of the first illumination light corresponding to the exposure condition defined in the defining the exposure condition process.

19. A fluorescence detecting apparatus comprising:
- an excitation light emitter for emitting: a first excitation light for exciting a fluorescent material within a measurement object to define an exposure condition and a second excitation light for exciting the fluorescent material within the measurement object;
- an illumination light emitter for emitting illumination light onto the measurement object;
- an image pickup device for sensing light from the measurement object; and
- a controller for controlling the image pickup device, the excitation light emitter, and the illumination light emitter, wherein the controller is operable to:
  - cause the excitation light emitter to emit the first excitation light onto the measurement object to define an exposure condition of the image pickup device, based on an image pickup result to be obtained by sensing light from the measurement object irradiated with the first excitation light by the image pickup device, so that a fluorescent portion of the measurement object excited by the second excitation light has a proper exposure condition of the image pickup device,
  - set a light amount of the illumination light to be emitted from the illumination light emitter depending on the exposure condition to make a fluorescent portion image clearly distinguished from a measurement object image, and
  - cause the excitation light emitter and the illumination light emitter to simultaneously emit the second excitation light, and the illumination light of the set light amount, to cause the image pickup device to sense light from the measurement object irradiated with the second excitation light and the illumination light.

* * * * *